United States Patent
Turovets

(10) Patent No.: US 11,260,013 B2
(45) Date of Patent: *Mar. 1, 2022

(54) COMPOSITIONS AND METHODS FOR PROVIDING HAIR GROWTH

(71) Applicant: MEDICELL TECHNOLOGIES, LLC, Carlsbad, CA (US)

(72) Inventor: Nikolay Turovets, Carlsbad, CA (US)

(73) Assignee: MediCell Technologies, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/318,103

(22) PCT Filed: Jul. 15, 2016

(86) PCT No.: PCT/US2016/042638
§ 371 (c)(1),
(2) Date: Jan. 15, 2019

(87) PCT Pub. No.: WO2018/013142
PCT Pub. Date: Jan. 18, 2018

(65) Prior Publication Data
US 2021/0093536 A1   Apr. 1, 2021

(51) Int. Cl.
*A61K 8/64*   (2006.01)
*A61Q 7/00*   (2006.01)

(52) U.S. Cl.
CPC . *A61K 8/64* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 2008/0050398 A1 | 2/2008 | Bockmuehl et al. | |
| 2017/0157015 A1* | 6/2017 | Turovets | A61Q 19/00 |
| 2021/0244794 A1* | 8/2021 | Turovets | A61K 38/1729 |

FOREIGN PATENT DOCUMENTS

| | | |
|---|---|---|
| CN | 102940631 | 2/2013 |
| WO | 2015195677 | 12/2015 |

OTHER PUBLICATIONS

Lough et al.,"Stimulation of the Follicular Bulge LGR5+ and LGR6+ Stem Cells with the Gut-Derived Human Alpha Defensin 5 Results in Decreased Bacterial Presence, Enhanced Wound Healing, and Hair Growth from Tissues Devoid of Adnexal Structures", Plastic and Reconstructive Surgery, vol. 132(5):1159-1171 (Year: 2013).*
PCT Search Report for PCT/US2016/042638 dated Apr. 11, 2017 in the name of Medicell Technologies, LLC and was filed on Jul. 15, 2019 (21 pages) and entitled Compositions and Methods for Providing Hair Growth.
Denver Lough et al., Stimulation of the Follicular Bulge LGR5+and LGR6+ Stem Cells with the Gut-Derived Human Alpha Defensin 5 Results in Decreased Bacterial Presence, Enhanced Wound Healing,and Hair Growth from Tissues Devoid of Adnexal Structures, Plastic and Reconstructive Surgery, vol. 132, Nov. 5, 1159-1171.
Sophie I. Candille et al., A B-Defensin Mutation Causes Black Coat Color in Domestic Dogs, Science. Nov. 30, 2007; 318(5855), 1418-1423.
Ali Mirabzadeh-Ardakani et al., Tissue- and age-dependent expression of the bovine DEFB103 gene and protein, Cell Tissue Res (2016) 363:479-490.

* cited by examiner

*Primary Examiner* — Anand U Desai
(74) *Attorney, Agent, or Firm* — Fish IP Law, LLP

(57) ABSTRACT

Compositions and methods for topical treatment of hair loss in otherwise normal skin that is affected by alopecia are presented. Such compositions include defensins in concentrations that are below those that exhibit antimicrobial activity, and can be in the form of a topically applied gel, lotion, wash, shampoo, cream, or mask. Various formulations for such compositions, which can include various pharmaceutically acceptable stabilizers, emollients, and fragrances, are provided. Such compositions and methods can be used in conjunction with traditional methods for treatment of hair loss.

16 Claims, No Drawings

COMPOSITIONS AND METHODS FOR PROVIDING HAIR GROWTH

FIELD OF THE INVENTION

The field of the invention is compositions and methods for hair growth, particularly compositions and methods that incorporate a defensin.

BACKGROUND

The following description includes information that may be useful in understanding the present invention. It is not an admission that any of the information provided herein is prior art or relevant to the presently claimed invention, or that any publication specifically or implicitly referenced is prior art. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Hair loss (i.e. alopecia) is a common condition that, while not life threatening, can result in considerable distress to those afflicted. The causes of hair loss are varied. Commonly associated with age, reasons for hair loss include androgen-induced alopecia (in both men and women), autoimmune disease (e.g. alopecia ariata), chemotherapy, and injury (including burns). Although the cosmetic impact of hair loss can be pronounced, it should be appreciated that loss of functional hair (for example, eyebrows and eyelashes) can result in considerable discomfort and inconvenience.

Hair loss can be concealed through the use of cosmetic devices. For example, artificial hairpieces can be used to cover an affected area. Such solutions are, however, limited. Production of hairpieces that faithfully mimic the appearance of hair-bearing skin has proven challenging, as have attempts to unobtrusively and securely affix such devices to the skin. The use of such devices necessarily covers the skin and interferes with normal function. Finally, hairpieces are not a suitable solution for some areas of the body (notably eyebrows and eyelashes).

Attempts have also been made to correct hair loss by transplantation of hair follicles (typically in the form of skin plugs) from hair-bearing skin to affected regions. In a typical procedure small plugs of skin bearing active hair follicles are removed from hair-bearing regions (for example, the sides and back of the scalp of a person with male pattern baldness) and implanted into affected regions. There are numerous drawbacks to such procedures, however. Great care must be taken in the placement of the grafts in order to avoid a patterned "doll hair" appearance, and such surgery comes with the risk of pain, infection, and scarring. In addition, many conditions that result in hair loss are progressive, and can result in the need for repeated procedures that draw on an ever diminishing supply of hair-bearing skin.

Some causes of hair loss can be addressed pharmaceutically. For example, alopecia ariata can be treated with some degree of success by suppression of the immune system. Good results, however, are not obtained in all patients, and there is a question of whether the risks of immune suppression are worthwhile for what is essentially a cosmetic, non-life threatening condition. Androgen-associated hair loss can be treated using compounds that suppress androgen production and/or conversion of testosterone to hydroxytestosterone (for example, a 5α-reductase inhibitor such as finasteride) however the side effects of such drugs can outweigh the benefit of improved appearance. More recently drugs such as minoxidil (a vasodilator used to treat hypertension) have been found to slow hair loss and provide a degree of hair re-growth of central hair in some patients with androgenic alopecia when applied topically. The mechanism by which minoxidil exerts this effect is not clear. Minoxidil is not, however, beneficial to all patients (with less than half of males responding) and must be used indefinitely. Minoxidil can also produce undesirable side effects, including burning sensations, growth of hair in unwanted areas, and can even cause hair loss in some individuals.

Stem cell therapy is finding increasing utility and acceptance in the treatment of a wide range of conditions. Lough et al (Plastic and Reconstructive Surgery, 132(5):1159-1171 (2013) have reported that human α-defensin 5 applied topically at antimicrobial concentrations to third degree burns results in stimulation of LGR5+ and LGR6+ stem cells, and produces improved healing with accompanying hair growth in a mouse model. It is not clear, however, that such affects could be obtained on unburned skin. Mirabzadeh-Ardakani et al (Cell Tissue Res. 363:479-490 (2016)) have noted that immunochemical staining indicates the presence of β-defensins near hair follicles. While it apparent that such defensins are present in proximity to hair follicles, their function and affect (if any) on the nearby follicle is not apparent.

Thus, there is still a need for safe and effective compositions and methods for treating hair loss in otherwise healthy skin.

SUMMARY OF THE INVENTION

The inventive subject matter is directed towards various topical formulations, methods of manufacture of the topical formulation in which the topical formulation includes antimicrobially effective or sub-antimicrobially effective concentrations of at least one defensin, and methods of applying the topical formulation to the skin of users to improve hair growth, modify hair color, and/or address gray hair in hair-bearing skin, including eyebrows, eyelashes, and skin affected by alopecia (for example, androgen induced alopecia or alopecia ariata) but is otherwise healthy.

In one aspect of the invention, a topical pharmaceutical formulation includes a defensin in a cosmetically acceptable carrier. Preferred topical pharmaceutical formulations are ready-to-use and contain the defensin at a sub-antimicrobially effective concentration, wherein the concentration is ineffective to inhibit growth of a microbial pathogen in a therapeutically effective manner but is effective in improving hair growth, modify hair color, and/or address gray hair in hair-bearing skin, including eyebrows, eyelashes, and skin that is affected by alopecia (for example, androgen induced alopecia or alopecia ariata) but is otherwise healthy. Still further preferred topical formulations may further comprise a blend of two or more different defensins, wherein the combined concentration of defensins in the formulation is a sub-antimicrobially effective concentration.

The inventors further contemplate methods of using defensins at antimicrobially effective or sub-antimicrobially effective concentrations in topical formulations to recruit LGR5+ and/or LGR6+ stem cells to an interfollicular space in non-injured skin. Methods of recruiting LGR5+ and/or LGR6+ stem cells can include a step of providing a topical formulation containing a sub-antimicrobial concentration of at least one defensin and a further step of applying the formulation to improve hair growth, modify hair color, and/or address grey hair in hair-bearing skin including eyebrows, eyelashes and skin that is affected by alopecia (for example, androgen induced alopecia or alopecia ariata) but is otherwise healthy.

It is preferred that the inventive compositions, methods, and uses employ at least one of an α-defensin, a β-defensin, a θ-defensin, α-defensin 1, α-defensin 5, α-defensin 6, neutrophil defensin 1, neutrophil defensin 2, neutrophil defensin 3, neutrophil defensin 4, β-defensin 1, β-defensin 2, β-defensin 3, β-defensin 4, plant defensins, and defensin-like peptides. In especially preferred topical compositions and methods, α-defensin 5 and/or β-defensin 3 are employed. It should be appreciated that the defensin can comprise a synthetic defensin, a human defensin, recombinant defensin, a primate defensin, a murine defensin, a caprine defensin, a bovine defensin, an ovine defensin, an equine defensin, a simian defensin, a lapine defensin, a porcine defensin, a canine defensin, a feline defensin, a plant defensin, and/or defensin-like peptides.

With respect to the sub-antimicrobially effective concentration of the first defensin in the ready-to-use topical pharmaceutical formulation, contemplated concentrations may be between 0.01 and 100 ng/ml, or between 1 and 30 ng/ml, including the end points of each range. Additionally, especially preferred embodiments of the inventive subject matter employ defensin concentrations of about 22 ng/ml and about 4.4 ng/ml in ready-to-use formulations.

The inventors unexpectedly found that, even at these low concentrations, defensins can be effective to improve hair growth, modify hair color, and/or address gray hair in hair-bearing skin including brows, eyelashes, and skin that is affected by alopecia (for example, androgen induced alopecia or alopecia ariata) but is otherwise healthy. Without wishing to be bound by any particular theory, the effectiveness of defensins at these sub-antimicrobially effective concentrations may be due to the activation and/or recruitment of LGR5+ and/or LGR6+ stem cells. Typically, defensins used in preferred embodiments of the inventive subject matter have a purity greater than 95% as shown by HPLC, and the sequence and proper disulfide bond formation of the defensins can be confirmed by tandem MS/MS.

Depending on the nature of the topical formulation, it should be recognized that defensins may be encapsulated in liposomes or other nanoparticles. In preferred formulations, defensins may also be associated with a carrier, in particular a protein carrier such as albumin (e.g., human serum albumin, bovine serum albumin, egg albumin, and recombinant albumin produced by rice, other plants, bacteria or yeast), also encapsulated in liposomes where desirable.

The inventors further contemplate that the topical pharmaceutical formulations may also include supplements to provide nutrition and support for LGR5+ and/or LGR6+ stem cells. Typical supplements include human serum albumin, bovine serum albumin, egg albumin (i.e. ovalbumin), recombinant albumin produced by rice, other plants, bacteria or yeast, plant hydrolysate, beta-cyclodextrin, glutamine, phospholipids, fibronectin, hyaluronate, hyaluronic acid, plant hydrolysate, L-alanyl-L-glutamine, gelatin, recombinant gelatin, Epidermal Growth Factor (EGF), vitamin E, Tocopheryl Nicotinate, ubiquinone, coenzyme Q10, and/or an antioxidant. Suitable pharmaceutical formulations can also incorporate an ultraviolet and/or visible light blocking or screening agent.

The inventors have appreciated that the topical pharmaceutical formulations of the inventive subject matter can be included in kits that can include an exfoliating mask. Especially preferred kits include a mask, a cream treatment formulation, and a serum treatment formulation. In addition, methods and compositions of the inventive concept can be used in conjunction with or to supplement traditional hair restoration therapies, including use of minoxifi, use of finasteride, and hair transplantation procedures.

Various objects, features, aspects and advantages of the inventive subject matter will become more apparent from the following detailed description of preferred embodiments.

DETAILED DESCRIPTION

The inventors unexpectedly discovered that sub-antimicrobial concentrations of defensins (for example, α-, β-, and/or θ-defensins) can achieve numerous desirable effects on non-injured skin when applied in ready-to-use topical formulations. Among other things, such topical formulations provide a significant growth and/or re-growth of hair from formerly hair-bearing but otherwise normal skin. Skin areas suitable for treatment include the scalp, eyebrows, eyelashes, beard, mustache, axillary, pectoral, pubic, and other body hair regions. This advantageously permits safe and effective treatment of conditions associated with a reduction or absence of hair from normally hair-bearing skin. Such conditions include androgen-induced alopecia (e.g. male pattern baldness), alopecia ariata, alopecia ariata universalis, post menopausal hair loss, and/or hair loss as a result of chemotherapy.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In one preferred embodiment, a ready-to-use topical pharmaceutical formulation comprises at least one defensin present in a topical pharmaceutical formulation at a sub-antimicrobially effective concentration. Suitable defensins include α-defensins, β-defensins, and/or θ-defensins. It should be appreciated that topical formulations can include one defensin, a combination of two defensins, or a combination of three or more defensins. The defensins used can be of the same or different types and/or subtypes. For example suitable defensin preparations can include one or more of α-defensin 1, α-defensin 5, α-defensin 6, neutrophil defensin 1, neutrophil defensin 2, neutrophil defensin 3, neutrophil defensin 4, θ-defensin, β-defensin 1, β-defensin 2, beta-defensin 3, β-defensin 4, plant defensins, and/or defensin-like peptides. Especially preferred topical formulations contain defensins of human origin, however the use of non-human defensins is contemplated. Such defensins can be isolated from natural sources, isolated from genetically modified cells (such as transformed bacteria, fungal, insect, avian, reptilian, and/or human cells), and/or can be generated by chemical synthesis. When two more defensins are used in combination, each defensin may be present in equal quantities by mass or at mass ratios specified to achieve a desired result, such as 1:1.5, 1:2, 1:4, 1:5, etc. Notably, it should be appreciated that the total concentrations of defensins used in contemplated ready-to-use formulations are ineffective at inhibiting substantial proliferation of microbes in established skin infections in a therapeutically effective manner. Alternatively, in other embodiments of the inventive concept the concentration of defensin or defensins comprising the formulation can be sufficient to have an anti-microbial effect.

As used herein, the term "ready-to-use" indicates that the defensin-containing topical formulation is in a form that is presented for sale and application. It is contemplated that ready-to-use formulations can comprise a fully combined solution, suspension, cream, gel, serum, lotion, etc. Alternatively, a defensin-containing preparation can be packaged in a separate container (e.g., in a vial that pumps a defensin solution with a cream that the user blends before applying to skin) and combined with another topical formulation at the time of use/application.

As also used herein, the phrase "sub-antimicrobially effective concentration" means concentration(s) of defensins which are characterized by an inability to inhibit the proliferation of microbes in an established infection. For example, a ready-to-use topical formulations can be formulated to not include defensin concentrations greater than 1 μg/ml. In preferred embodiments, the concentration of defensins lies between about 0.01 and about 100 ng/ml, and even more typically between about 1 and about 30 ng/ml. It should be appreciated that within this application contemplated concentrations include the end points of each range. In even more preferred embodiments, the topical pharmaceutical or cosmetic formulations have defensin concentrations between about 22 ng/ml and about 4.4 ng/ml. As used herein, when the term "about" is used in conjunction with a numeral, "about" means a range of plus or minus ten percent of the numerical value given, including end points. The recitation of ranges of values herein is merely intended to serve as a shorthand method of referring individually to each separate value falling within the range. Unless otherwise indicated herein, each individual value is incorporated into the specification as if it were individually recited herein.

General topical formulations can include any and all formulations suitable for pharmaceutical and/or cosmetic topical use, particularly on non-injured skin. As used herein, the term "non-injured" skin refers to skin in which dermis and hypodermis have not been subjected to a burn or similarly traumatic injury and are substantially intact. Therefore, viewed from a different perspective, non-injured skin will appear intact to the unaided eye, with no breach sufficiently large or deep to result in bleeding. Thus, non-injured (or "healthy") skin can include normally hair-bearing skin with reduced or absent active hair follicles that is otherwise healthy, aged skin, and skin with first degree burn, environmental exposure, bruising, or partially ablated stratum corneum. Non-injured (or healthy) skin also excludes skin displaying persistent infection with pathogens that result in visible symptoms and signs of infection.

With respect to the source of defensins, the inventors contemplate that defensins from both natural and synthetic sources may be suitable for incorporation into topical formulations. For example, defensins can be obtained from plants (e.g., *Arabidopsis*, pea, tobacco, spruce, and/or recombinant plants), mammals or other animals, recombinant organisms (such as yeast, bacteria, or cultured cells), and/or products of laboratory peptide synthesis (for example, through the use of a Merrifield resin or other solid-phase synthesis). Exemplary defensins derived from natural sources may include human defensins, simian or primate defensins, murine defensins, bovine defensins, ovine defensins, caprine defensins, equine defensins, lapine defensins, porcine defensins, canine defensins, and/or feline defensins.

Due to their relatively low quantities generally present in unmodified organisms and low molecular weight, it is preferred that the defensins are obtained through synthesis. Such synthetic defensins can include defensins produced by chemical synthesis (e.g., solid phase synthesis) or by recombinant technologies (e.g., produced by recombinant or otherwise genetically modified bacteria, yeast, cultured cells, cultured tissue, plants, and/or animals). The inventors further contemplate that defensin analogs such as hapivirins and diprovirins can be used in some embodiments of the inventive subject matter. Still further, the inventors contemplate that defensins utilized in embodiments of the inventive concept can be modified to increase their activity and specificity for induction of hair growth. For example, defensins may have amino acid sequences that are modified from that of a native defensin, and/or can be denatured and re-natured under controlled conditions to generate a desired disulfide bond formation and/or arrangement (which can be monitored by MS analysis and/or CD spectroscopy). Alternatively, chemical modifications (e.g., substitution with non-naturally occurring amino acids and/or PEGylation to increase half-life time, and/or derivatization of proteinogenic amino acids to increase lipophilicity) are contemplated to tailor the activity and/or stability of defensins of a formulation of the inventive concept.

Regardless of the source of the defensins, it should be appreciated that specific activity of a defensin is dependent on various factors, including isomeric form and tertiary structure of the final protein. Thus, and especially where the defensin is synthetic, orthogonal protecting groups can be used to protect selected cysteine residues, which can then be individually deprotected and bonded with the matching target cysteine residue, leading to coordinated non-random disulfide bond formation. Use of such protecting groups in the synthetic strategy can give rise to defensins with a specific activity that is comparable to the specific activity of the native defensin. Any suitable characterization and quality control measures may be employed. Typically, the specific activity of defensins incorporated into the inventive topical formulations is measured by purity as determined by HPLC. In exemplary embodiments, the defensin is between about 80% and about 100% pure, more typically the defensin is at least about 90% pure, or at least about 95% pure, or at least about 99% pure, or at least about 99.9% pure. Absence of contaminating partial products along with proper amino acid sequence and disulfide bond formation can be confirmed by tandem MS/MS, for example.

With respect to suitable concentration of defensins in formulations presented herein, it is contemplated that all concentrations are deemed appropriate so long as such concentrations are effective in providing hair growth in normally hair-bearing skin that has an absence or reduced number of active hair follicles but is otherwise healthy. Consequently, the total concentration of defensins (single type or combination of distinct defensins) in the final cosmetic formulation as applied to the skin can be between about 0.01 ng/ml and about 100 ng/ml, or between about 0.1 ng/ml and about 100 ng/ml, or between about 1 ng/ml and about 100 ng/ml, or between about 2 ng/ml and about 80 ng/ml, or between about 4 ng/ml and about 60 ng/ml, or between about 1 ng/ml and about 30 ng/ml. Thus, preferred compositions include defensins at a concentration of at least about 0.01 ng/ml, at least about 0.1 ng/ml, at least about 1 ng/ml, or at least about 4 ng/ml, but no more than about 200 ng/ml, no more than about 100 ng/ml, no more than about 75 ng/ml, or no more than about 50 ng/ml.

In some embodiments a defensin can be associated with one or more other protein(s) to improve stability and/or delivery characteristics (i.e. carrier protein(s)). In this context, it should be appreciated that such an association is preferably non-covalent (e.g., electrostatic, ionic, hydrophobic, etc.), however, covalent attachment to a side group of the protein is not excluded. Exemplary proteins include lactoferrin, transferrin, and albumin (e.g., human serum albumin, bovine serum albumin, ovalbumin, and/or recombinant albumin). The defensins and protein carriers can be in various ratios, including equimolar, sub-, and supramolar ratios. Additionally, combinations of two or more carrier proteins can be used. For example, in a formulation in which two defensins are used, one defensin may be associated with one carrier protein, and the other defensin may be associated with a different carrier protein. Therefore, any combination of defensins and carriers is contemplated.

In still further contemplated aspects, one or more defensin(s) (and/or carrier protein(s)) can be encapsulated in cosmetically acceptable formulations, particularly formulations having a lipid membrane. For example, liposomes, microcapsules, nanocapsules, microparticles, nanoparticles, microparticle delivery systems, are especially contemplated. A description of some cosmetically acceptable cosmetic delivery systems can be found in Maherani et al, "Liposomes: A Review of Manufacturing Techniques and Targeting Strategy," Current Nanoscience; 7:436-452 (2011). A preferred method of liposome manufacturing is a shear method. Preferred delivery systems resemble naturally occurring membranes, are flexible, and can penetrate interstitial spaces between cells. It is further contemplated that such delivery systems can have monolayer, bilayer (e.g. unilammellar vesicle or ULV), or multi layer structures (e.g. multilamellar vesicle or MLV). Additionally, multilayer liposomes, microcapsules, microsomes, and nanocapsules can have nested structures (e.g. multivesicular vesicle or MVV). Such vesicle elements of suitable delivery systems used in the topical formulations can range in size from about 500 nm to about 10 μm. In the preparation of delivery systems, all pharmaceutically and/or cosmetically acceptable lipid compositions are contemplated, especially pharmaceutically acceptable lipids. In most instances preferred cosmetic delivery systems comprise amphipathic or amphiphilic molecules such as phospholipids or combinations of phospholipids (e.g., phosphatidylcholine, phosphatidylethanolamine, phosphatidic acid, phosphatidylserine, and phosphoinositides). Additionally, in some instances contemplated delivery systems can include additive(s) such as sterols, polyethylene glycol, cholesterol, dicethylphosphate, stearyl amine, etc. With respect to the amount of delivery systems incorporated in each ready-to-use formulation, delivery system content will typically be adjusted to achieve a sub-antimicrobial concentration of defensins within a preferred range. Unilamellar vesicles/liposomes can be produced using high shear techniques. Such vesicles have a greater Zeta Potential than a typical liposome, which allows for smaller, more uniform particle size and increased stability. Zeta Potential is an indicator of the electronic charge on the surface of any macroscopic material that is in contact with a liquid. This can be used to predict and control the stability of suspensions. The higher the Zeta Potential, the greater the stability of the suspended particles or vescicles as the charged particles are able to repel and overcome their innate tendency to aggregate.

It should be noted that defensins, protein carriers, liposomes, or other membranaceous structures have a molecular weight that exceeds transmembrane delivery, and even delivery across the stratum corneum. Nevertheless, the inventors have surprisingly found that the defensins preparations discussed herein have a profound effect on hair growth, possibly through modulation of stem cell activity in dermal and hypodermal layers. While not wishing to be bound by any theory or hypothesis, the inventors contemplate that the liposomal formulations have the ability to transport the defensins via an interstitial route and/or to invade the hair follicle to a depth and reach and/or accumulate to a concentration sufficient to activate LGR5+ and/or LGR6+ cells. Viewed from another perspective the use of the described delivery systems may aid in the delivery of defensins, as it is not expected that defensins alone can penetrate the stratum corneum of the skin (which act as a barrier to molecules with molecular weights greater than 500 Da). Moreover, when associated with albumin (65-70 kDa) and/or liposomes, it becomes at least conceptually even more difficult for a defensin composition to penetrate unbroken skin. Thus, the inventors hypothesize that the mechanism for delivering defensins is different in unbroken skin when compared with broken or injured skin.

In some embodiments of the inventive concept a formulation that includes one or more defensins can be delivered by an active mechanism. Suitable active mechanisms can include application of laser energy, thermal energy, acoustic pressure waves, ultrasound, microneedles, and/or injections to the skin area undergoing treatment, in order to facilitate transport of the defensins to the desired region of the skin and/or skin-associated (i.e. epidermis, dermis, basal layer, and/or hair follicle) area(s). For example, a skin region to be treated can be treated by dermabrasion techniques (such as application of sugar crystals, cellulosic plant matter, frozen $CO_2$, polymeric beads, and/or silica granules), by manual application or as part of a fluid flow. Similarly, a skin region to be treated with a defensin can be prepared by application of chemical agents that reduce the thickness or increase the permeability of the stratum corneum, such as surfactants and/or chemical reductants. In another embodiment, skin can be prepared by the application of pulsed laser light and/or acoustic energy (e.g. via ultrasound) prior to or with application of a defensin. Similarly, skin can be prepared through the use of a mechanical device, such as scraping with a blade, application of a microneedle patch, and/or use of a roller device equipped with sharp protrusions. The thickness of the skin to be treated with a defensin can also be reduced using stripping techniques (such as the application and subsequent removal of an adhesive film, tape, or wax) prior to application of a defensin. Skin can be treated with a defensin-containing composition prior to, during, and/or following such skin preparative treatments. For example, skin preparative treatments as described above can be applied prior to application of a defensin-containing composition. Alternatively, skin preparative treatments as described above can be applied following application of a defensin-containing preparation to the skin. In another embodiment, a skin preparative treatment can be applied to the skin during the same time period that a defensin-containing composition is being applied to the skin. In still other embodiments a skin preparative treatment can be applied over a time period that encompasses or overlaps two or more of a time period prior to application of a defensin-containing composition to the skin, a time period during which a defensin-containing composition is applied to the skin, and/or a time period following application of a defensin-containing composition to the skin. Such skin preparative treatment can be applied in a continuous or discontinuous fashion.

In another aspect, a formulation of the inventive concept can provide additional components that nourish and support stem cells in treated skin. For example, albumin (e.g., human serum albumin, bovine serum albumin), egg albumin (ovalbumin), recombinant albumin, plant hydrolysate, and β-cyclodextrin, glutamine, phospholipids (liposomes), fibronectin, hyaluronate, plant hydrolysate, L-alanyl-L-glutamine, gelatin, Vitamin E (tocopheryl nicotinate), ubiquinone (coenzyme Q10), gelatin, recombinant gelatin, hyaluronic acid, Epidermal Growth Factor can provide nutrition and support to such stem cells.

In yet further contemplated aspects, topical treatment of hair-depleted but otherwise healthy skin using defensin preparations can be further assisted by supplemental procedures. Especially contemplated procedures include chemical and/or mechanical exfoliation. For example, chemical exfoliation may be performed using one or more proteases (for example papain, *Lactobacillus*/Pumpkin Ferment Extract, *Lactobacillus/Punica Granatum* Fruit Ferment Extract, etc).

Although not wishing to be bound by theory, the inventors contemplate that the inventive subject matter (i.e., methods and use of antimicrobially effective or sub-antimicrobially active concentrations of defensins in topical formulations) can act to recruit LGR5+ and/or LGR6+ stem cells to the interfollicular space of non-injured skin, which in turn fosters and supports the growth of hai, possibly by secretion of activating and/or trophic factors by such stem cells into the interfollicular space. Most typically, a user will be instructed to apply the topical formulation to regions of non-injured skin that is normally hair-bearing but is currently hairless or shows reduced hair growth, under a protocol effective to induce hair growth and/or prevent additional hair loss. For example, defensins can be applied at least once daily (or twice daily) for a period of at least one week, or two weeks, three weeks, six weeks, or even longer. Beneficially, the total quantity of applied formulations is such that the formulation is absorbed into the skin. For example, topical formulations are typically applied at about 0.1 to about 500 mg per $cm^2$, about 0.1 to about 500 mg per $cm^2$, about 0.5 to about 300 mg per $cm^2$, about 5 to about 500 mg per $cm^2$, or about 100 to about 500 mg per $cm^2$.

Using topical compositions such as those presented in the examples below, the inventors have surprisingly found that formulations that included the defensins are effecting in promoting the growth of hair from non-injured skin.

In some embodiments of the inventive concept, topical application of such defensin formulations on a suitable schedule is sufficient to reduce the area of skin showing an absence of hair or reduced hair growth to less than 90%, 80%, 70%, 60%, 50%, 40%, 30%, 20%, 10%, 5%, or less than 5% of the area of skin showing an absence of hair or reduced hair growth prior to treatment with the topical defensin formulation. In other embodiments of the inventive concept, topical application of such a defensin formulation on a suitable schedule can increase hair growth in a treated skin area by more than 300%, 200%, 100%, 50%, 25%, or 10% of hair growth associated with untreated skin adjacent to or in an area otherwise comparable to the treated skin area.

In suitable treatment protocols the defensin formulation can be applied four times a day (e.g. every 6 hours), three times a day (e.g. every 8 hours), twice a day (e.g. every 12 hours), once a day (e.g. in the morning), every other day, every three days, once a week, or at a frequency determined through practical use. In some embodiments the topical defensin formulation can be applied more frequently at the beginning of treatment. In other embodiments the topical defensin formulation can be applied more frequently as treatment progresses. In still other embodiments treatment can continue on a first treatment schedule until hair growth in the treated skin area is normal, acceptable, and/or is stabilized and improved, and then switched to a second treatment schedule that maintains the treated appearance.

Treatment with the taught topical defensin formulations can be carried out for any period of time suitable to provide re-growth of hair and/or prevent additional hair loss. Suitable treatment periods can be at least a week, 2 weeks, 3 weeks, 4 weeks, 6 weeks, 8 weeks, 3 months, 4 months, 5 months, 6 months, or longer. In some embodiments a topical defensin formulation can be applied on a long term (i.e. greater than one year) or for an open ended time period on a maintenance schedule suitable to provide re-growth of hair and/or prevent additional hair loss.

Formulations and methods of the inventive concept can also be applied in concert with traditional methods of hair restoration. For example, defensin preparations can be used as described above in addition to or in concert with drugs that reduce androgen production and/or production of 5-hydroxytestosterone, or alternatively can be used in concert with immunosuppressant drugs used in the treatment of alopecia ariata. Similarly, defensin preparation of the inventive concept can be used in concert with topical medications such as minoxidil.

In some embodiments, formulations and methods of the inventive concept can be used to supplement or potentiate surgical interventions used to treat alopecia. For example, formulations and methods of the inventive concept can be applied to a skin area following a hair transplantation procedure in order to improve hair growth in the treated area and/or reduce or eliminate the "shedding" period that accompanies such a transplant procedure. Alternatively (or in addition) formulations and methods of the inventive concept can be applied to a skin area prior to the performance of a hair transplant procedure on that area in order to improve hair growth and/or reduce or eliminate the shedding period that accompanies hair transplantation. Similarly, in some embodiments of the inventive concept hair plugs that have been extracted from hair-bearing skin areas can be treated with one or more defensins (for example, by contact with a solution or suspension containing one or more defensins) prior to implantation in order to improve hair growth and/or reduce or eliminate the shedding period that accompanies the transplant procedure. Such treatment can be provided by immersion of removed follicle-bearing skin plugs in a defensin-containing solution for a suitable period of time (e.g. greater than 5 minutes) prior to implantation. Alternatively such treatment can be provided by applying a mist or spray of a defensin-containing solution to removed follicle-bearing skin plugs prior to implantation.

It should be appreciated that a defensin can be selected to affect one or more stages of hair growth in order to provide the desired effect. For example, a defensin can be selected to increase the length of the anagen phase, during which active hair growth takes place. Alternatively, a defensin can be selected to reduce the length of the catagen phase, and/or to delay its onset. In still other embodiments a defensin can be selected to reduce the length of the telogen phase, and/or delay its onset.

In some embodiments of the inventive concept the defensin preparation is formulated and/or configured for application to different hair-bearing regions of the body. For example, a defensin preparation intended for use on the scalp can be formulated using a defensin preparation that is suitable for use with scalp hair, and/or can be provided as a shampoo or spray that is readily applied to large areas. In another embodiment, a defensin preparation intended for use on an eyebrow region can be formulated using a defensin preparation that is suitable for use with brow hair, and provided as a lotion or gel having sufficient viscosity to keep the preparation localized at the brow region. Similarly, a defensin preparation intended for use on an eyelash region (i.e. the margin of the eyelid) can be selected for use with lash hair and provided as a highly viscous gel or paste, with an applicator supplied to direct the placement of the defensin preparation and reduce the incidence of accidental placement in the eye. Defensin preparation intended for use in the restoration of facial hair can be selected for use with beard and/or mustache hair, and be provided as a mask formulation that serves to retain the defensin on the desired skin areas.

In some embodiments of the inventive concept, defensin preparations can be utilized to alter the pigmentation of existing hair in addition to or instead of use in restoring hair to hair-depleted regions of skin that is affected by alopecia but otherwise healthy. Without wishing to be bound by theory, the inventors believe that factors released by LGR5+ and/or LGR6+ stem cells can stimulate growth, multiplication, and or activity of melanocytes associated with hair follicles. Alternatively, such defensins may directly or indirectly affect the activity of enzymes involved in melanogenesis. For examples, a topical defensin preparation can be used to darken gray or white hair associated with aging or vitiligo. In another embodiment, a topical defensin preparation can be used to darken blonde, red, or brown hair to a darker shade. In such embodiments a defensin preparation can be applied to the entire scalp, or to a portion of the scalp in order to achieve a desired cosmetic effect.

Examples

Suitable formulations are described in International Patent Application No. PCT/US15/36049, which is incorporated herein by reference. While suitable formulations can be prepared using any number of ingredients and formulations known in the art, preferred topical formulations include those that are ready-to-use and can be applied by a user. Therefore, with respect to pharmaceutically and/or cosmetically acceptable carriers, all pharmaceutically and/or cosmetically acceptable carriers are contemplated and include creams, oil-in-water emulsions, water-in-oil emulsions, foams, mousses, ointments, lotions, suspensions, serum, and gels. In some embodiments the cosmetic formulation can include a sunscreen, such as an ultraviolet and/or visible light blocking ingredient (for example, zinc oxide), which advantageously reduces the impact of UV exposure on stem cells.

Examples of suitable topical cream formulations can include one or more of the following ingredients: water, *Carthamus tinctorius* (safflower) oleosomes, *Butyrospermum parkii* (Shea) Butter, *Macadamia integrifolia* seed oil, niacinamide, yeast extract, ammonium acryloyldimethyltaurate/VP copolymer, *Helianthus annuus* (sunflower) seed oil, phospholipids, alpha-defensin 5, beta-defensin 3, hyaluronic acid, *Ophiopogon japonicus* root extract, hydrolyzed *Candida saitoana* extract, sea whip extract, *Lycium chinense* fruit extract, *Vaccinium angustifolium* fruit extract, *Vaccinium marcrocarpon* (cranberry) fruit extraubiquinone, L-alanyl-L-glutamine, *Leuconostoc*/Radish root ferment filtrate, gelatin, SH oligopeptide-1, xanthan gum, phytic acid, polysorbate 20, caprylic/capric triglyceride, phenoxyethanol, caprylyl glycol, ethylhexylglycerin, hexylene glycol, potassium sorbate, sodium chloride, and natural and/or artificial fragrance.

Examples of a suitable topical serum formulation can include one or more of the following: water, cyclopentasiloxane, glycerin, niacinamide, *Sinorhizobium meliloti* ferment filtrate, dimethicone, polysorbate 20, dimethicone/vinyl dimethicone crosspolymer, lauryl PEG-9 polydimethylsiloxyethyl dimethicone, ammonium acryloyldimethyltaurate/VP copolymer, phospholipids, alpha-defensin 5, beta-defensin 3, palmitoyl tripeptide-38, sodium hyaluronate, *Arabidopsis thaliana* extract, sea whip extract, ergothioneine, *Helianthus annuus* (sunflower) seed oil, *Rosmarinus offinalis* (rosemary) leaf extract, SH oligopeptide-1, tocopheryl acetate, ubiquinone, *Leuconostoc*/radish root ferment filtrate, albumin, gelatin, L-alanyl-L-glutamine, caprylic/capric triglyceride, cetyl hydroxyethylcellulose, lecithin, hydroxypropyl cyclodextrin, phytic acid, phenoxyethanol, caprylyl glycol, ethylhexylglycerin, hexylene glycol, and/or sodium chloride.

Examples of a suitable mask formulation can include one or more of the following: butylene glycol, PEG-8, tapioca starch, sucrose, titanium dioxide, hydroxyethyl acrylate/sodium acryloyldimethyl taurate copolymer, squalane, polysorbate 60, *Carica papaya* (*papaya*) fruit, papain, *Aloe barbadensis* leaf juice, *Lactobacillus*/pumpkin ferment extract, *Lactobacillus*/*Punica granatum* fruit germent extract, sea whip extract, *Cananga odorata* flower oil, *Citrus aurantium dulcis* (orange) peel oil, caprylic/capric triglyceride, lactic acid, phenoxyethanol, caprylyl glycol, ethylhexylglycerin, and/or hexylene glycol.

Liposome Formulations

Table 1 below shows an exemplary liposome delivery formulation including two types of defensins. Such liposomes are typically incorporated into a formulation at a fraction of about 1.0 wt % to 10.0 wt % for most topical applications. In some embodiments defensin concentration can be up to 10 mg/ml or higher.

TABLE 1

Exemplary Liposome Formulation

| Component | Concentration |
|---|---|
| Water (protease-free) | to 100% |
| Albumin | 0.1-1.0 mg/ml |
| L-alanyl-L-glutamine | 0.1-1.0 mg/ml |
| Gelatin | 2-200 µg/ml |
| Matrix proteins | 1-100 ng/ml |
| Human α-defensin 5 | 1-200 ng/ml |
| Human β-defensin 3 | 1-200 ng/ml |
| Growth factors (e.g., EGF, FGF-2), optional | 0.1-100 ng/ml |
| Phospholipids | 2-20 wt % |
| Antioxidants | 0.3-3 wt % |

In another embodiment of the inventive subject matter a suitable topical formulation can be provided as a kit. Preferred kits can include a mask formulation and a defensin-containing cream or serum treatment formulation suitable for use with the mask formulation. Even more preferred kits can include a mask formulation and both a defensin-containing cream formulation and a defensin-containing serum formulation.

In the manufacture of cosmetic defensin formulations, it is contemplated that concentrated defensin preparations can be added to pharmaceutically and/or cosmetically suitable vehicle base formulations such that the concentration of the defensin in the ready-to-use product is at a targeted sub-antimicrobially effective concentration. Depending on the desired formulation, defensins can be incorporated into concentrated preparations as solutions, associated with carrier proteins, and more typically as liposomal formulations. Such concentrated defensin preparations can be added to pharmaceutically and/or cosmetically acceptable base formulations in proportions as given below:

Exemplary Body Lotion (Oil-in-Water) Formulation:

| Mixture A | PEG-7 hydrogenated castor oil | 2.00% |
|---|---|---|
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol, methylparaben, ethylparaben, butylparaben, propylparaben, isobutylparaben | 0.30% |
| Mixture B | water, distilled | 73.40% |
| | phenoxyethanol, methylparaben, ethylparaben, butylparaben, propylparaben, isobutylparaben, | 0.30% |
| | glycerin | 3.00% |
| Mixture C | concentrated defensin preparation | 5.00% |
| Mixture D | acrylamides copolymer, mineral oil C13-C14 isoparaffin, polysorbate 85 | 3.00% |

To prepare a body lotion formulation Mixture A is melted at approximately 70° C. Mixture B is heated to approximately 70° C. and then added to Mixture A while stirring to produce an intermediate lotion. Stirring is continued until the intermediate lotion has cooled down to approximately 30° C. Mixture C and Mixture D are added to the cooled intermediate lotion while stirring, and the resulting mixture is the homogenized. In some embodiments final defensin concentrations can range from 1 ng/ml to 10 mg/ml or higher.

Exemplary Gel-Lotion Formulation:

| Mixture A | acrylamides copolymer, mineral oil, C13-14 isoparaffin, polysorbate 85 | 5.00% |
|---|---|---|
| | myreth-3 myristate | 4.00% |
| Mixture B | water, distilled | 85.00 |
| | phenoxyethanol (and) methylparaben (and) ethylparaben (and) butylparaben (and) propylparaben (and) isobutylparaben | 0.50% |
| | xanthan gum | 0.50% |
| Mixture C | concentrated defensin preparation | 5.00% |

To prepare the gel lotion formulation Mixture A is heated to approximately 50° C. Mixture B is dispersed at room temperature and the added to the heated Mixture A while stirring to form an intermediate gel-lotion. The intermediate gel lotion is cooled to about 30° C., then Mixture C is added while stirring.

Exemplary Oil-in-Water Cream Formulation:

| Mixture A | cetearyl alcohol (and) ceteareth-20 | 8.00% |
|---|---|---|
| | cocoglycerides | 2.00% |
| | cetearyl alcohol | 2.00% |
| | dicaprylyl ether | 8.00% |
| | oleyl erucate | 7.00% |
| | phenoxyethanol, methylparaben, ethylparaben, butylparaben, propylparaben, isobutylparaben | 0.30% |
| Mixture B | water, distilled | 62.40% |
| | phenoxyethanol, methylparaben, ethylparaben, butylparaben, propylparaben, isobutylparaben | 0.30% |
| | glycerin | 5.00% |
| Mixture C | concentrated defensin preparation | 5.00% |

To prepare the formulation Mixture A is melted at approximately 70° C. Mixture B is heated to approximately 70° C. and added to Mixture A while stirring to form an intermediate cream. Stirring is continued until the intermediate cream has cooled to approximately 30° C. Mixture C is added while stirring and the resulting cream is homogenized. In some embodiments final defensin concentration can range from 1 ng/ml to 10 mg/ml or higher.

Exemplary Water-in-Oil Cream Formulation:

| Mixture A | diisostearoyl polyglyceryl-3 dimer dilinoleate | 3.00% |
|---|---|---|
| | beeswax | 0.60% |
| | castor oil, hydrated | 0.40% |
| | paraffinum subliquidum | 5.00% |
| | isohexadecane | 10.00% |
| | PPG-15 stearyl ether | 2.00% |
| | dimethicone | 0.50% |
| | phenoxyethanol, methylparaben, ethylparaben, butylparaben, propylparaben, isobutyparaben | 0.30% |
| Mixture B | water, distilled | 68.40% |
| | phenoxyethanol, methylparaben, ethylparaben, butylparaben, propylparaben, isobutylparaben | 0.30% |
| | glycerin | 3.00% |
| | $MgSO_4 \cdot 7H_2O$ | 1.00% |
| Mixture C | concentrated defensin preparation | 5.00% |
| Mixture D | silica dimethyl silylate | 0.50% |

To prepare the oil in water cream formulation Mixture A is heated to approximately 80° C. Mixture B is brought to about 80° C. and then added to Mixture A while stirring to form an intermediate cream. Stirring is continued until the intermediate cream has cooled down to approximately 30° C., then Mixture C and Mixture D are added and the resulting cream homogenized. In some embodiments final defensin concentration can range from 1 ng/ml to 10 mg/ml or higher.

Exemplary Shampoo Formulation:

| | |
|---|---|
| Sodium polyoxyethylene lauryl ether sulfate | 15.0% |
| Alkyl polyglucoside | 4.0% |
| N-ethanol-N-methyl dodecanoic acid amide | 3.0% |
| EDTA-Na$_2$ | 0.3% |
| Malic acid to adjust pH to 6.0 | q.s. |
| Preservative | 0.5% |
| Concentrated defensin preparation | 10.0% |
| Purified water | balance |

To prepare the shampoo formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

Exemplary Body Wash Formulation:

| | |
|---|---|
| Sodium polyoxyethylene lauryl ether sulfate | 16.0% |
| Sodium polyoxyethylene | 5.0% |
| N-ethanol-N-methyl palm kernel oil fatty acid Amide | 2.5% |
| Glycerin | 3.0% |
| Cationized cellulose | 0.1% |
| Ethylene glycol distearate | 3.0% |
| EDTA-Na$_2$ | 0.3% |
| Citric acid to adjust pH to 5.7 | q.s. |
| Preservative | 0.5% |
| Concentrated defensin preparation | 7.5% |
| Purified water | balance |

To prepare the body wash formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

Exemplary Face Wash Formulation:

| | |
|---|---|
| Sodium polyoxyethylene lauryl ether sulfate | 20.0% |
| N-ethanol-N-methyl dodecanoic acid amide | 4.8% |
| Glycerin | 3.0% |
| Hydroxyethyl cellulose | 0.3% |
| Ethylene glycol distearate | 1.5% |
| EDTA-Na$_2$ | 0.3% |
| Citric acid to adjust pH to 6.0 | q.s. |
| Preservative | 0.5% |
| Concentrated defensin preparation | 10.0% |
| Purified water | balance |

To prepare the face wash formulation all ingredients are mixed together and the volume is brought to about 90 ml. The pH is then adjusted and the volume is finally adjusted to 100 ml (all percentages are weight %). In some embodiments final defensin concentration can range from 1 ng/ml to 10 mg/ml or higher.

Inventors have observed and have received reports that application of defensin-containing formulations (as described above) to previously hair-bearing skin in which hair density has been lost or reduced has resulted in significant re-growth of hair in these regions (data not shown). The inventors have also observed and have received reports of modification and/or improvements in the pigmentation of hair in skin regions so treated, particularly in hypopigmented (e.g. gray or white hair). These results are achieved in various different hair-bearing regions of the body, including eyebrows. The new hair thus generated has a natural appearance, distribution, and density, is cosmetically appealing, and is enduring. This hair growth was achieved without notable side effects.

Inventors have also observed and received reports of improvement of the results of conventional hair restoration treatments, particularly hair transplant surgery, when used in conjunct with methods and compositions of the inventive concept. For example, the shedding period that characteristically follows hair transplantation can be reduced by 10%, 20%, 30%, 40%, 50%, 60%, 70% 80%, 90%, more than 90%, or completely eliminated by application of compositions of the inventive concept prior to, during, and/or following a hair transplant procedure. Similarly, overall hair loss during a post-hair transplantation shedding period can be reduced by 10%, 20%, 30%, 40%, 50%, 60%, 70% 80%, 90%, more than 90%, or completely eliminated by application of compositions of the inventive concept prior to, during, and/or following a hair transplant procedure.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, for example not A plus N, or B plus N, etc.

What is claimed is:

1. A topical pharmaceutical formulation, comprising:
a pharmaceutically acceptable carrier in combination with a first defensin, wherein the first defensin is alpha-defensin 5;
wherein the first defensin is present in the topical pharmaceutical formulation at a concentration selected to provide growth of hair in intact hair-bearing skin affected by hair loss and that is otherwise healthy, and wherein the topical pharmaceutical formulation is a ready-to-use topical pharmaceutical formulation.

2. The topical pharmaceutical formulation of claim 1, wherein the concentration of the first defensin in the ready-to-use topical pharmaceutical formulation is between 0.01 and 100 ng/ml, inclusive.

3. The topical pharmaceutical formulation of claim 1, wherein the first defensin is associated with a protein carrier.

4. The topical pharmaceutical formulation of claim 1, further comprising a second defensin, wherein the second defensin is different from the first defensin, and wherein the second defensin is present in the topical pharmaceutical formulation at a antimicrobially effective or sub-antimicrobially effective concentration.

5. The topical pharmaceutical formulation of claim 1, further comprising a supplement for LGR5+ or LGR6+ stem cells, wherein the supplement comprises at least one of human serum albumin, recombinant albumin, bovine serum albumin, egg albumin, plant hydrolysate, beta-cyclodextrin, glutamine, phospholipids, fibronectin, hyaluronate, hyaluronic acid, epidermal growth factor, fibroblast growth factor, plant hydrolysate, L-alanyl-L glutamine, gelatin, recombinant gelatin, vitamin E, Tocopheryl Nicotinate, Coenzyme Q10, and ubiquinone.

6. A method of recruiting LGR5+ or LGR6+ stem cells to an interfollicular space in non-injured skin, comprising:
providing a topical formulation comprising a first defensin at a concentration effective to increase hair growth in intact hair-bearing skin that is affected by alopecia and is otherwise healthy, wherein the first defensin is alpha-defensin 5; and
instructing a user to apply the topical formulation to intact, non-injured skin under a protocol effective to increase hair growth in hair-bearing skin that is affected by alopecia and is otherwise healthy.

7. The method of claim 6, wherein the concentration of the first defensin in the topical formulation is between 0.01 and 100 ng/ml, inclusive.

8. The method of claim 6, wherein the topical formulation further comprises a second defensin, wherein the second defensin is different from the first defensin, and wherein the second defensin is present in the topical formulation at an antimicrobially effective or sub-antimicrobially effective concentration.

9. The method of claim 6, wherein alopecia is selected from the group consisting of androgen associated alopecia, alopecia ariata, and alopecia ariata universalis.

10. The method of claim 6, comprising delivery of the first defensin to skin and/or skin-associated tissues using a device selected from the group consisting of a laser, acoustic pressure wave device, ultrasound device, a microneedle, and a hypodermic needle.

11. A method of increasing hair growth in intact hair-bearing skin that is affected by alopecia and is otherwise healthy comprising:
identifying an individual in need of treatment for alopecia;
providing a topical formulation comprising a first defensin at a concentration effective to recruit LGR5+ or LGR6+ stem cells to an interfollicular space in non-injured skin, wherein the first defensin is alpha-defensin 5; and
applying the topical formulation to intact, non-injured skin of the individual under a protocol effective to increase hair growth in hair-bearing skin that is affected by alopecia and is otherwise healthy.

12. The method of claim 11, wherein the concentration of the first defensin in the topical formulation is between 0.01 and 100 ng/ml, inclusive.

13. The method of claim 11, wherein the topical formulation further comprises a second defensin, wherein the second defensin is different from the first defensin, and wherein the second defensin is present in the formulation at an antimicrobially effective or a sub-antimicrobially effective concentration.

14. The method of claim 11, comprising delivery of the first defensin to skin and/or skin-associated tissues using a device selected from the group consisting of a laser, acoustic pressure wave device, ultrasound device, a microneedle, and a hypodermic needle.

15. The method of claim 11, wherein the method is used in conjunction with a supplementary treatment method comprising at least one of the group consisting of use of finasteride, use of minoxidil, and a hair transplant procedure.

16. The method of claim 11, comprising applying to topical formulation by topical application to the surface of intact, non-injured skin.

* * * * *